(12) United States Patent
Yang et al.

(10) Patent No.: US 7,949,411 B1
(45) Date of Patent: May 24, 2011

(54) EPICARDIAL LEAD

(75) Inventors: Michael Yang, Thousand Oaks, CA (US); Sheldon Williams, Green Valley, CA (US); Wenbo Hou, Lancaster, CA (US); Kevin L. Morgan, Simi Valley, CA (US); Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 373 days.

(21) Appl. No.: 11/626,132

(22) Filed: Jan. 23, 2007

(51) Int. Cl.
*A61N 1/05* (2006.01)

(52) U.S. Cl. ........................................ 607/122

(58) Field of Classification Search .............. 607/5, 119, 607/122
See application file for complete search history.

(56) References Cited

U.S. PATENT DOCUMENTS

| | | | |
|---|---|---|---|
| 4,030,509 A | 6/1977 | Heilman et al. | |
| 4,142,530 A | 3/1979 | Wittkampf | |
| 4,235,246 A | 11/1980 | Weiss | |
| 4,299,239 A | 11/1981 | Weiss et al. | |
| 4,567,900 A | 2/1986 | Moore | |
| 4,620,550 A | 11/1986 | Doroshuk | |
| 4,860,769 A * | 8/1989 | Fogarty et al. | 607/119 |
| 4,865,037 A | 9/1989 | Chin et al. | |
| 4,991,578 A | 2/1991 | Cohen | |
| 4,991,603 A | 2/1991 | Cohen et al. | |
| 4,998,975 A * | 3/1991 | Cohen et al. | 607/5 |
| 5,052,407 A | 10/1991 | Hauser et al. | |
| 5,143,090 A | 9/1992 | Dutcher et al. | |
| 5,217,028 A | 6/1993 | Dutcher et al. | |
| 5,336,252 A | 8/1994 | Cohen | |
| 5,387,233 A | 2/1995 | Alferness et al. | |
| 5,387,234 A | 2/1995 | Hirschberg | |
| 5,397,342 A | 3/1995 | Heil, Jr. et al. | |
| 5,397,343 A | 3/1995 | Smits | |
| 5,425,756 A | 6/1995 | Heil, Jr. et al. | |
| 5,653,734 A | 8/1997 | Alt | |
| 5,716,382 A | 2/1998 | Snell | |
| 5,803,928 A * | 9/1998 | Tockman et al. | 607/122 |
| 5,871,532 A | 2/1999 | Schroeppel | |
| 5,897,586 A * | 4/1999 | Molina | 607/129 |
| 5,928,278 A | 7/1999 | Kitschmann | |
| 5,974,341 A | 10/1999 | Er et al. | |
| 6,539,944 B1 | 4/2003 | Watson | |
| 6,687,549 B1 | 2/2004 | Helland et al. | |
| 6,718,212 B2 | 4/2004 | Parry et al. | |
| 6,837,848 B2 | 1/2005 | Bonner et al. | |
| 2003/0040787 A1 | 2/2003 | Flynn et al. | |
| 2003/0074041 A1 | 4/2003 | Parry et al. | |
| 2003/0114908 A1 | 6/2003 | Flach | |

(Continued)

FOREIGN PATENT DOCUMENTS

| WO | 2004011081 A1 | 2/2005 |
|---|---|---|
| WO | 2005046789 A1 | 5/2005 |
| WO | 2005092431 A1 | 10/2005 |

OTHER PUBLICATIONS

NonFinal Office Action, mailed May 12, 2009—Related U.S. Appl. No. 11/669,797.

(Continued)

*Primary Examiner* — Eric D. Bertram

(57) ABSTRACT

Embodiments include electrical leads and methods of using electrical leads that may be used for delivering both cardioversion/defibrillation signals and pacing signals and sensing to target tissue. Some of these embodiments may also be used to sense and transmit electrical signals from target tissue. Some electrical lead embodiments are configured to be delivered into a patient's intrapericardial space by non-invasive methods.

23 Claims, 16 Drawing Sheets

U.S. PATENT DOCUMENTS

| | | |
|---|---|---|
| 2004/0054391 A1 | 3/2004 | Wildon |
| 2004/0127967 A1 | 7/2004 | Osypka |
| 2004/0267338 A1 | 12/2004 | Harrison |
| 2005/0102010 A1 | 5/2005 | Lau et al. |
| 2005/0102011 A1 | 5/2005 | Lau et al. |
| 2005/0102012 A1 | 5/2005 | Lau et al. |
| 2005/0102014 A1 | 5/2005 | Lau et al. |
| 2005/0113900 A1 | 5/2005 | Shiroff et al. |
| 2005/0288715 A1 | 12/2005 | Lau et al. |
| 2006/0009831 A1 | 1/2006 | Lau et al. |

OTHER PUBLICATIONS

Final Office Action, mailed Jan. 4, 2010—Related U.S. Appl. No. 11/669,797.

D'Avila, Andre MD et al., "Pericardial Anatomy for the Interventional Electrophysiologist, " J Cardiovasc Electrophysiol. Apr. 2003, 14:422-430.

* cited by examiner

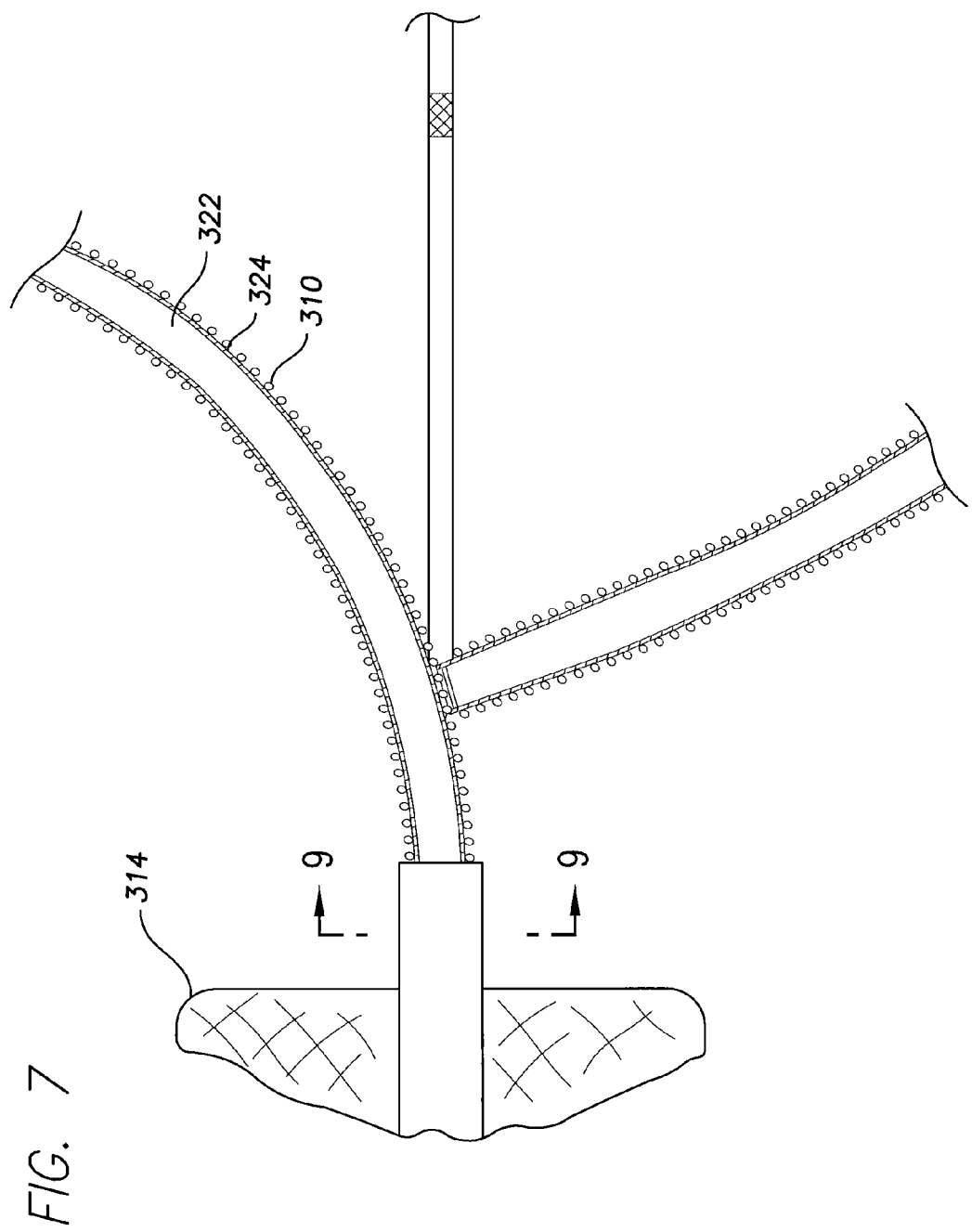

EPICARDIAL LEAD

FIELD OF THE INVENTION

Embodiments of the present invention generally relate to implantable medical devices such as implantable electrical stimulation devices including pacemakers, implantable cardioverter/defibrillators (ICDs) and the like. In particular, embodiments of the invention are directed to electrical leads that couple output signals of stimulation devices such as pacemakers, ICDs and the like to target tissue to be stimulated.

BACKGROUND

Body implantable electrical leads form the electrical connection between stimulation devices, such as a cardiac pacemaker or ICD, and target body tissue, such as that of the heart, which is to be electrically stimulated. The leads connecting stimulation devices with the heart may generally be used for cardioversion, defibrillation, pacing or sensing electrical signals produced by the heart. Some electrical leads may be used for both pacing and sensing of electrical signals from target tissue in which case a single electrical lead serves as a bi-directional pulse transmission link between a stimulation device and the heart. An endocardial electrical lead which is inserted into a vein and guided therethrough into a cavity or chamber of the heart includes at its distal tip an electrode designed to contact the endocardium. Such an electrical lead may further include a proximal end carrying an electrical connector assembly adapted to be received by a receptacle in a stimulation device. A flexible cable or coil conductor surrounded by an insulating sheath may be used to couple a terminal contact on the electrical connector assembly with the electrode at the distal tip.

To prevent displacement or dislodgment of the tip electrode and to maintain the necessary stable electrical contact between the tip electrode and the endocardial tissue, the electrode must be firmly anchored relative to the tissue. To achieve this, one type of lead, sometimes referred to as an active fixation lead, includes a pointed, extendable/retractable helix adapted to be screwed into the heart tissue to be stimulated. In this fashion, the position of the tip electrode is mechanically stabilized by positively anchoring the lead tip so that it remains securely in place during the lifetime of the implant.

The fixation helix may itself comprise the tip electrode in which case it is electrically coupled by means of a coil conductor to a rotatable terminal contact pin on the connector assembly. Rotational torque applied to the connector pin at the proximal end of the lead is transmitted via the coil conductor to the helix electrode which is thereby screwed into the heart tissue. Removal of the screw-in electrode from the endocardium is effected by counter-rotation of the connector pin. Thus, in electrical leads having a screw-in helix electrode, the coil conductor is used not only as a conductor for electrically coupling the connector pin and the helix electrode, but also as a tool for extending or retracting the helix electrode relative to the distal end of the lead during lead fixation or removal by rotating the connector pin.

Such conventional electrical leads are an important element of implantable stimulation devices and the like. Current electrical lead designs are adequate in many respects, however, they can be difficult to remove and often do not provide sufficient surface area contact of the electrodes for some indications. In particular, the area of tissue engaged by a helix electrode is limited by the outer diameter of the lead header. In addition, the helix electrode is limited to a single point of tissue contact for electrical stimulation. What has been needed are electrical leads for electrical stimulation devices that are readily deployed to a variety of locations within a patient's body, and particularly, a variety of locations around a patient's heart, and reliably secured to target tissue if necessary. What has also been needed are electrical leads that may be used to provide multiple tissue contact points, electrodes having varying surface areas for different purposes, or both of these features for electrical stimulation signal delivery upon deployment.

SUMMARY

Some embodiments of an implantable electrical lead include an elongate flexible lead body having a distal end, a distal portion and an inner lumen extending therethrough. A resilient distal loop extends from the distal end of the lead body and is configured to resiliently resume a looped shape after being straightened for deployment within a patient's body. The distal loop has a shaping lumen extending through at least one side of the distal loop in fluid communication with the inner lumen of the lead body with a stop disposed in and blocking a distal portion of the shaping lumen. A distal electrode is disposed on the distal loop and has sufficient surface area for delivering shocking pulses of electrical energy to a human patient's heart. A proximal connector is disposed at a proximal end of the lead body and has a conductive terminal and an inner lumen in fluid communication with the inner lumen of the lead body. An elongate conductor is disposed and in electrical communication between the distal electrode and a conductive terminal disposed on the proximal connector.

Some embodiments of a system for deploying an implantable electrical lead in a patient's pericardial space include an implantable electrical lead with an elongate flexible lead body having a distal end, a distal portion and an inner lumen extending therethrough, The lead also has a resilient distal loop disposed at a distal end of the lead body configured to resiliently resume a looped shape after being straightened for deployment within the patient's body and has a shaping lumen extending through one side of the distal loop in fluid communication with the inner lumen of the lead body with a stop disposed within the shaping lumen at a distal portion of the distal loop. A distal electrode is disposed on the distal loop having sufficient surface area for delivering shocking pulses of electrical energy to the patient's heart and a proximal connector is disposed at a proximal end of the lead body having a conductive terminal and an inner lumen in fluid communication with the inner lumen of the lead body. An elongate conductor is disposed and in electrical communication between the distal electrode and a conductive terminal disposed on the proximal connector. The system also includes a stylet which has a blunt distal end and is configured to slide into the inner lumen of the connector, lead body and shaping lumen of the distal loop and has a resistance to bending sufficient to straighten the distal loop for deployment.

Some embodiments of an implantable electrical lead include an elongate flexible lead body having a distal end, a distal portion and a longitudinal axis. A resilient distal loop is disposed at a distal end of the lead body and is configured to resiliently resume a looped shape after being straightened for deployment within a patient's body and has a shaping lumen extending through at least one side of the distal loop. A distal electrode is disposed on the distal loop and has sufficient surface area for delivering shocking pulses of electrical energy to a patient's heart. A first pacing electrode having a small surface area relative to the distal electrode is disposed radially outward from the longitudinal axis of the distal portion of the lead body in a direction substantially perpendicular to a plane of the distal loop. A second pacing electrode having a small surface area relative to the distal electrode is disposed radially outward from the longitudinal axis of the distal portion of the lead body in a direction substantially perpendicular to a plane of the distal loop and opposite that of the first pacing electrode. Some embodiments may include a second pacing electrode having a surface area substantially equal to or less than the surface area of the distal electrode. A proximal connector is disposed at a proximal end of the lead body and has a conductive terminal corresponding to each electrode and an inner lumen in fluid communication with the inner lumen of the lead body. Elongate conductors are disposed and in electrical communication between the distal electrode, the first pacing electrode, the second pacing electrode and respective conductive terminals disposed on the proximal connector.

Some embodiments of a method of applying therapeutic electrical energy to target tissue of a patient include disposing a distal end and distal port of an introducer sheath into the pericardial space of a patient's heart. A stylet is advanced into a shaping lumen of an electrical lead which includes an elongate flexible lead body with a distal end, a distal portion and an inner lumen, a resilient distal loop extending distally from the distal end of the lead body having a shaping lumen extending through one side of the distal loop and a stop disposed in a distal portion of the shaping lumen, a distal electrode disposed on the distal loop having sufficient surface area for delivering shocking pulses of electrical energy to the patient's heart, a proximal connector disposed at a proximal end of the lead body, and an elongate conductor member disposed and in electrical communication between the distal electrode and a conductive terminal disposed on the proximal connector. Once the stylet is disposed in the shaping lumen, a distal end of the electrical lead is advanced through the introducer sheath and into the patient's intrapericardial space and a therapeutic electrical signal is transmitted from a stimulation device in electrical communication with the electrical lead to the target tissue of the patient in contact with the distal electrode. For some embodiments, the electrical lead further includes a tissue attachment element and the method further includes advancing the distal end of the electrical lead into the pericardial space until the tissue attachment element is disposed within the pericardial space and allowing body tissue of the patient to attach to the tissue attachment element. For some embodiments, disposing the distal end and distal port of an introducer sheath into the pericardial space of a patient's heart includes advancing a needle through the patient's chest and into a pericardial space of the patient's heart, advancing a guidewire through an inner lumen of the needle into the pericardial space and advancing a dilator and introducer sheath over the guidewire and into the pericardial space of the patient's heart. Thereafter, the dilator and guidewire are withdrawn from the introducer sheath.

Some embodiments of a method of applying therapeutic electrical energy to target tissue of a patient include disposing a distal end and distal port of an introducer sheath into the pericardial space of a patient's heart. A stylet is advanced into a shaping lumen of an electrical lead including an elongate flexible lead body having a distal end and a distal portion, a resilient distal loop extending from the distal end of the lead body having a shaping lumen extending through one side of the distal loop, a distal electrode disposed on the distal loop having sufficient surface area for delivering shocking pulses of electrical energy to the patient's heart, a first pacing electrode disposed radially outward from the longitudinal axis of the distal portion of the lead body in a direction substantially perpendicular to a plane of the distal loop, a second pacing electrode disposed radially outward from the longitudinal axis of the distal portion of the lead body in a direction substantially perpendicular to a plane of the distal loop and opposite that of the first pacing electrode, a proximal connector disposed at a proximal end of the lead body and an elongate conductor members disposed and in electrical communication between the electrodes and respective conductive terminals disposed on the proximal connector. Once the stylet is disposed within the shaping lumen, the distal end of the electrical lead is advanced through the introducer sheath and into the patient's pericardial space and a therapeutic electrical signal is transmitted from a stimulation device in electrical communication with the electrical lead to the target tissue of the patient in contact with the distal electrode. For some embodiments, the conduction of each pacing electrode is tested and the pacing electrode with better electrical communication with an epicardial surface of the patient selected for pacing. The other pacing lead that is not selected for pacing may be used for sensing. For some embodiments, the electrical lead further includes a tissue attachment element and the method further includes advancing the distal end of the electrical lead into the pericardial space until the tissue attachment element is disposed within the pericardial space and allowing body tissue of the patient to attach to the tissue attachment element. For some embodiments, disposing the distal end and distal port of an introducer sheath into the pericardial space of a patient's heart includes advancing a needle through the patient's chest and into a pericardial space of the patient's heart, advancing a guidewire through an inner lumen of the needle into the pericardial space and advancing a dilator and introducer sheath over the guidewire and into the pericardial space of the patient's heart. Thereafter, the dilator and guidewire are withdrawn from the introducer sheath.

These features of embodiments will become more apparent from the following detailed description when taken in conjunction with the accompanying exemplary drawings.

BRIEF DESCRIPTION OF THE DRAWINGS

FIG. 3 is a block diagram of portions of an embodiment of an external programmer for use in processing and displaying event codes, counters, IEGM signals and the like.

FIG. 7 is an enlarged view in section of the encircled area 7-7 of FIG. 5.

DETAILED DESCRIPTION

Embodiments discussed herein relate to cardiac pacing methods, cardiac sensing methods and associated devices designed to relieve a variety of conditions that result from cardiac disease as well as other conditions. In order to pace or otherwise impart electrically delivered therapy to a patient's tissue, such as heart tissue, an electrical lead or delivery system is typically required. An electrical lead is used to deliver a therapeutic signal from a stimulation device to a target tissue site of the patient's body. Following is a general discussion of stimulation device embodiments that may be used with electric lead and stimulation method embodiments discussed herein.

Overview of Stimulation Device Embodiments

Figure 1:
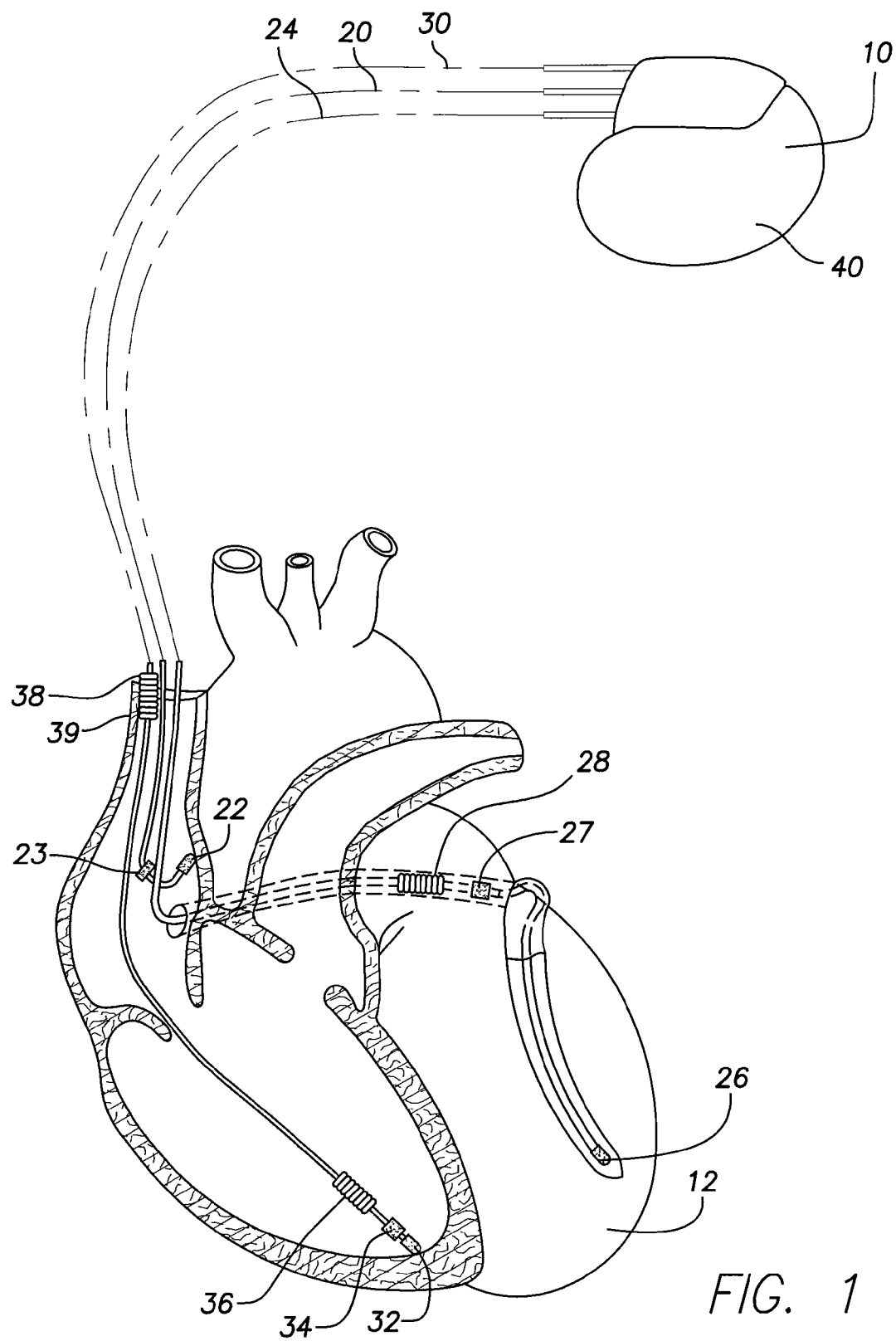
FIG. 1 is a simplified diagram illustrating an implantable cardiac stimulation device in electrical communication with at least three electrical leads implanted into the heart of a patient.

FIG. 1 shows a stimulation device 10 in electrical communication with the heart 12 of a patient with three electrical leads, 20, 24 and 30, in a configuration suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. As ventricular overdriving or pacing may be an effective way to induce effective preconditioning of a patient's myocardium, the left ventricular tip electrode 26 is positioned so as to provide such pacing to the left ventricle.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava 39. Accordingly, the right ventricular lead 30 is capable of receiving cardiac signals, and delivering stimulation in the form of pacing and shock therapy to the right ventricle.

Figure 2:
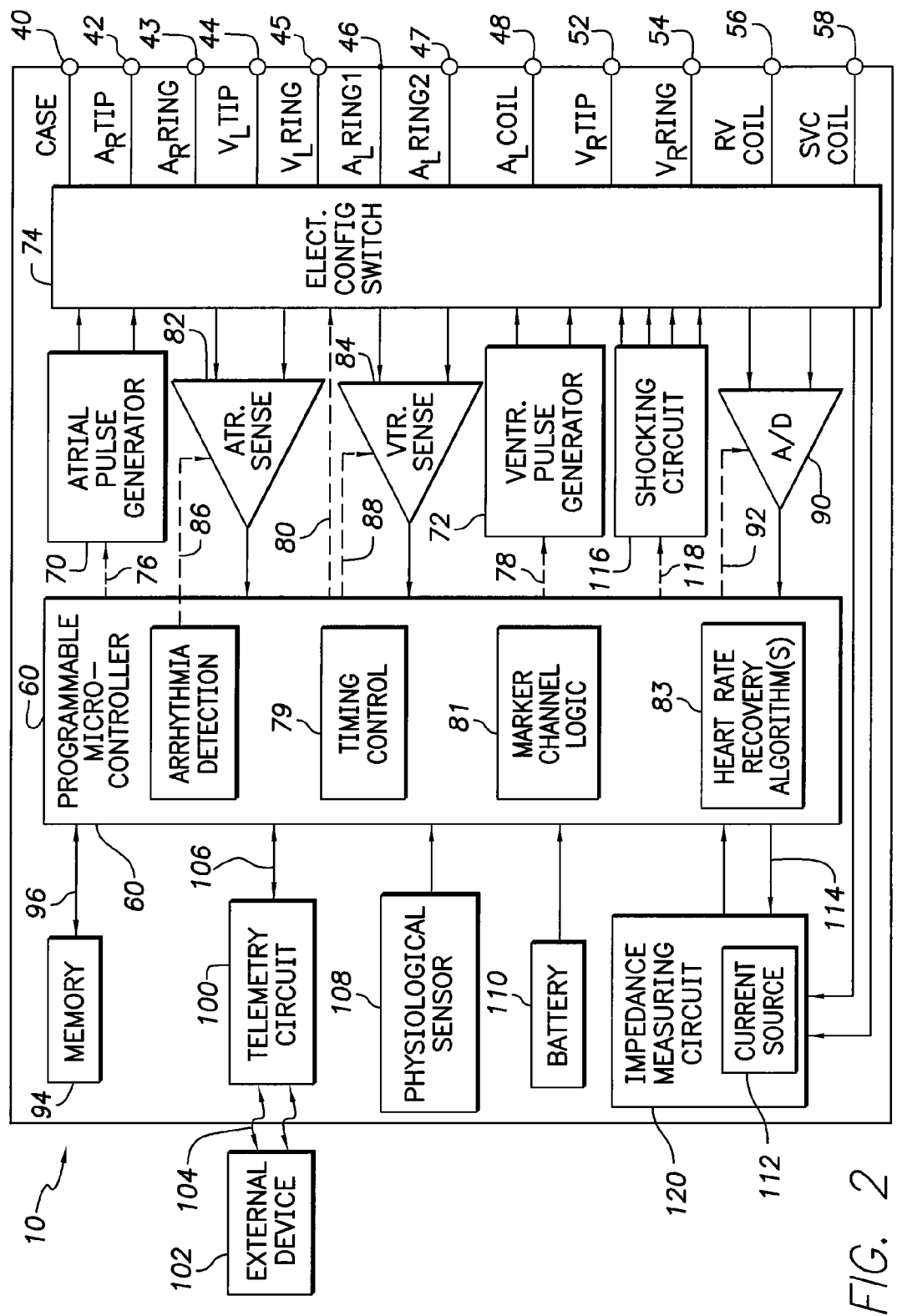
FIG. 2 is a functional block diagram of a multi-chamber implantable stimulation device illustrating exemplary basic elements of a stimulation device which can provide cardioversion, defibrillation, and/or pacing stimulation in up to four chambers of the heart.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and appropriate circuitry may be duplicated, eliminated or disabled in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (Rv COIL)

56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a controller in the form of a programmable microcontroller 60, which controls the various modes of stimulation therapy. The microcontroller 60 (also referred to herein as a controller or control unit) includes a microprocessor, or equivalent control circuitry, designed specifically for detecting sensed cardiac function data, generating warning signals that may be felt, heard or seen by a patient, controlling delivery of stimulation therapy as well as other function and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. Microprocessor-based control circuits for performing timing and data analysis functions may be used.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 also includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown). Moreover, as the explained in greater detail below, the microcontroller transmits signals to the switch 74 to connect a set of electrodes during a far-field overdrive pacing algorithm and a different set of electrodes during a near-field overdrive pacing algorithm. The microcontroller further includes an arrhythmia detector.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the stimulation device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia or other clinical condition. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals may also be applied to the inputs of an analog-to-digital (A/D) data acquisition system 90. The data acquisition system 90 may be configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart 12 within each respective tier of therapy. Other pacing parameters include base rate, rest rate and circadian base rate.

The operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104. In some embodiments, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Such information may also be used to trigger initiation, cessation or modification of a preconditioning stimulation signal. Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

External Programmer

Figure 3:
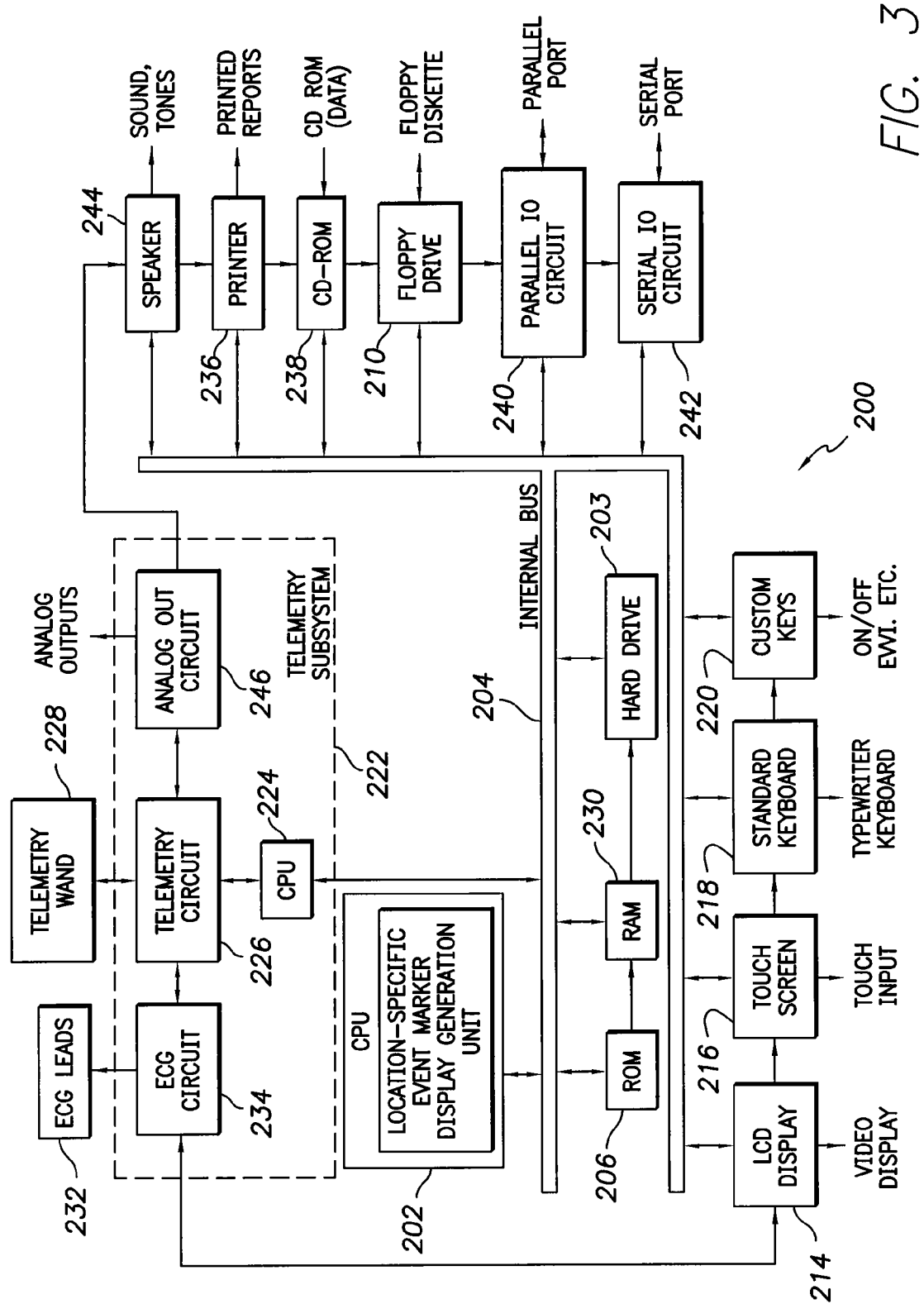

FIG. 3 illustrates pertinent components of an external programmer 200 for use in programming an implantable cardiac stimulation device such as the stimulation device 10 of FIGS. 2 and 3. Such programmer embodiments permit a physician or other user to program the operation of the implanted stimulation device 10 and to retrieve and display information received from the implanted device 10 such as IEGM data and device diagnostic data. In particular, the programmer 200 is provided with internal components capable of separately receiving, storing and processing event markers representative of events paced or sensed in any of the four chambers of the heart. Additionally, the external programmer 200 receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Operations of the programmer 200 are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an EWI key.

Typically, the physician initially controls the programmer 200 to retrieve data stored within the implanted cardiac stimulation device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via the internal bus. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device.

Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Preferably, all data stored within the implanted device is recorded within "event records" which facilitate the efficient storage and transmission of the data. The data provided by the stimulation device 10 and the event markers displayed by the external programmer 200 distinguish among a greater number of sensing locations, such as between the left and right chambers of the heart or among multiple locations within a single chamber of the heart.

For some embodiments, the memory of the external programmer 200 stores the location-specific event records, counter data and IEGM data for each of the four chambers of the heart received from the stimulation device 10. ROM 206 stores location-specific event records, counter data and IEGM data for each of the four chambers of the heart. A location-specific event marker display generation unit within the CPU controls the generation of graphic displays of diagnostic information based on the location-specific event records, counter data and IEGM data stored in ROM 206. The location-specific event processing unit may be a software module of a control program executed by the CPU.

Data retrieved from the implanted stimulation device 10 is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device 10 may be further controlled to transmit additional data in real time as it is detected by the implanted device 10, such as additional IEGM data, lead impedance data, and the like. Additionally, or in the alternative, telemetry subsystem 222 receives ECG signals from ECG leads 232 via an ECG processing circuit 234. As with data retrieved from the implanted stimulation device 10 itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time.

Thus the programmer 200 receives data both from the implanted device 10 and from the external ECG leads. Data retrieved from the implanted device 10 includes parameters representative of the current programming state of the implanted device. Under the control of the physician, the external programmer 200 displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted cardiac stimulation device may be found in U.S. Pat. No. 5,716,382 entitled "Programmer for an Implantable Cardiac Stimulating Device" (Snell), filed Aug. 2, 1995, which is incorporated by reference herein in its entirety. Prior to reprogramming specific parameters, the physician may control the external programmer to display any or all of the data retrieved from the implanted device or from the ECG leads, including displays of ECGs, IEGMs, and statistical patient information. In particular, the external programmer can be controlled to generate graphic displays or printouts of location-specific; IEGMs and event markers.

Depending upon the programming of the external programmer and the commands entered, the programmer may display either a single combined IEGM representative of a combination of the IEGM signals from the four chambers of the heart or may display the individual IEGM signals separately. Further information pertaining to information that may be displayed using the programmer may be found in U.S. Pat. No. 5,974,341 entitled "Method and Apparatus for Detecting and Displaying Diagnostic Information in Conjunction With Intracardiac Electrograms and Surface Electrocardiograms" (S. Er et al.), filed Dec. 22, 1997, which is incorporated by reference herein in its entirety. Any or all of the information displayed by programmer 200 may also be printed using a printer 236.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a serial port 240 or a parallel port 242. Other peripheral devices may be connected to the external programmer via serial port 240 or a parallel port 242 as well. Although one of each is shown, a plurality of input output (IO) ports may be provided. A speaker 244 is included for providing audible tones to the user, such as a warning beep in the event the physician provides improper input. Telemetry subsystem 222 additionally includes an analog output circuit 246 for controlling the transmission of analog output signals.

With the programmer 200 configured as shown, a physician or other user operating the external programmer is capable of retrieving, processing and displaying a wide range of information received from the ECG leads or from the implanted device and to reprogram the implanted device 10 if needed. The descriptions provided herein with respect to FIG. 4 are intended merely to provide an overview of the operation of programmer 200 and are not intended to describe in detail each and every feature of the hardware and software of the device and is not intended to provide an exhaustive list of the functions performed by the device.

Electrical Lead Embodiments

The general discussion of the stimulation device 10 above has been made with reference to various electrical leads having a substantially conventional configuration. However, in some cases, it may be desirable to use an electrical lead for delivery of a variety of therapeutic and sensing signals that may be deployed by non-invasive methods to target sites within a patient's body, such as the pericardial space of a patient's heart.

Figure 4:
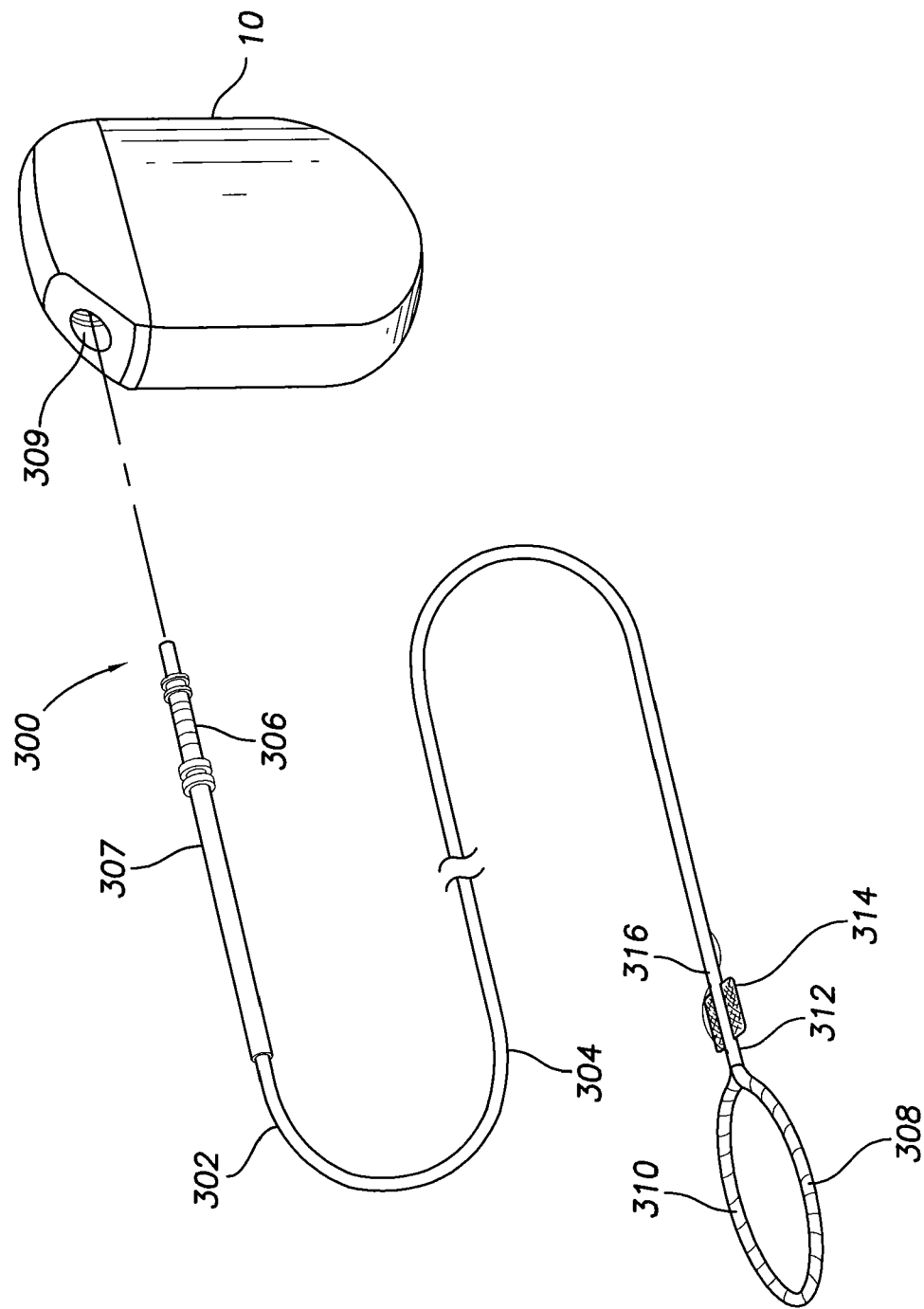
FIG. 4 is an exploded perspective view of an embodiment of a system for delivering therapeutic electric signals to tissue of a patient.

FIG. 4 illustrates a system 300 for delivering electrical stimulation energy to target tissue a patient including shocking and pacing signals to the patient's heart. In addition, the system 300 is configured to receive sensed signals generated by target tissue of the patient's heart. The system 300 includes stimulation device 10 and an electrical lead 302 having an elongate flexible lead body 304 and a connector 306 that is disposed on a proximal end 307 of the lead body 304. The connector 306 is configured to plug into a mating receptacle 309 of the stimulation device 10. A distal loop 308 having a distal electrode 310 disposed thereon extends from a distal end 312 of the lead body 304. A tissue fixation element 314 is disposed on a distal portion 316 of the lead body 304 and may include a flat piece or pieces of porous material that lie substantially in a same plane as the distal loop 308.

Referring to FIGS. 5-9, the electrical lead 302 of FIG. 4 is shown in more detail. The implantable electrical lead includes the elongate flexible lead body 304 having a longitudinal axis 317 and a multi-lumen shaft member 318. The multi-lumen shaft member 318 has a main inner lumen 320 extending the length thereof which is in fluid communication with a shaping lumen 322 of the distal loop 308. The resilient distal loop 308 has a closed configuration that extends distally from the distal end 312 of the lead body 304 and is configured to resiliently resume a looped shape after being straightened for deployment within a patient's body.

The shaping lumen 322 extends through at least one side of the distal loop 308 which is configured to accept a stylet that may be used to straighten the distal loop 308 for delivery through a lumen of a tubular member, such as an introducer sheath, to target tissue. The shaping lumen 322 for the embodiment shown is disposed within a tubular member 324 that extends through the circumference of the distal loop 308. The shaping lumen 322 may optionally have a stop 325 disposed within a distal portion 326 of the shaping lumen 322 for controlling distal advancement of a stylet being inserted into the shaping lumen 322. For some embodiments, the distal loop 308 lies substantially within a plane when in a relaxed non-deformed state. The circumference of some embodiments of the resilient distal loop 308 may be about 100 mm to about 400 mm.

Figure 5:
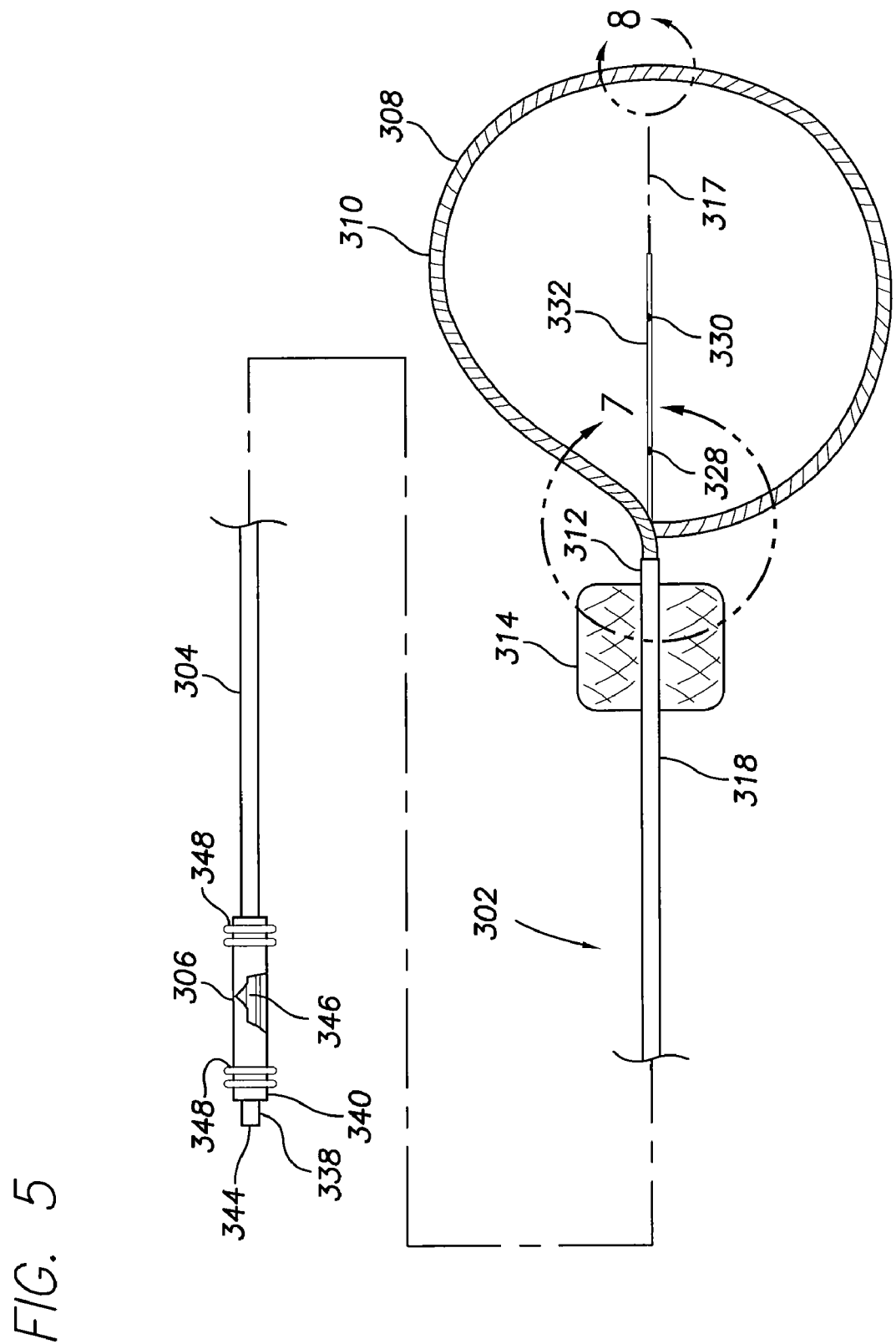
FIG. 5 is a top view of an embodiment of an electrical lead.
Figure 6:
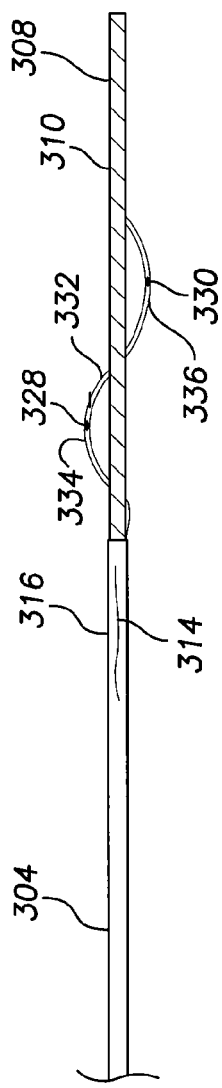
FIG. 6 is a side view of a distal portion of the electrical lead of FIG. 5.
Figure 9:
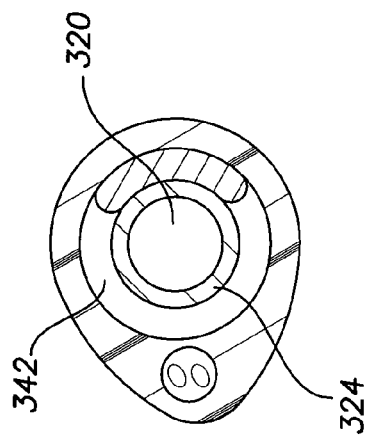
FIG. 9 is a transverse cross sectional view of the electrical lead taken along lines 9-9 in FIG. 7.
Figure 8:
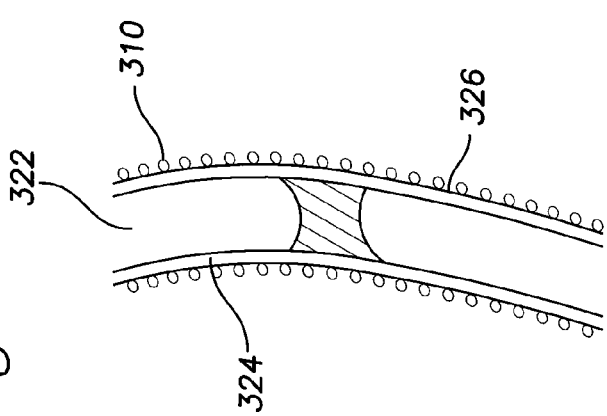
FIG. 8 is an enlarged view in section of the encircled area 8-8 in FIG. 5.
Figure 10:
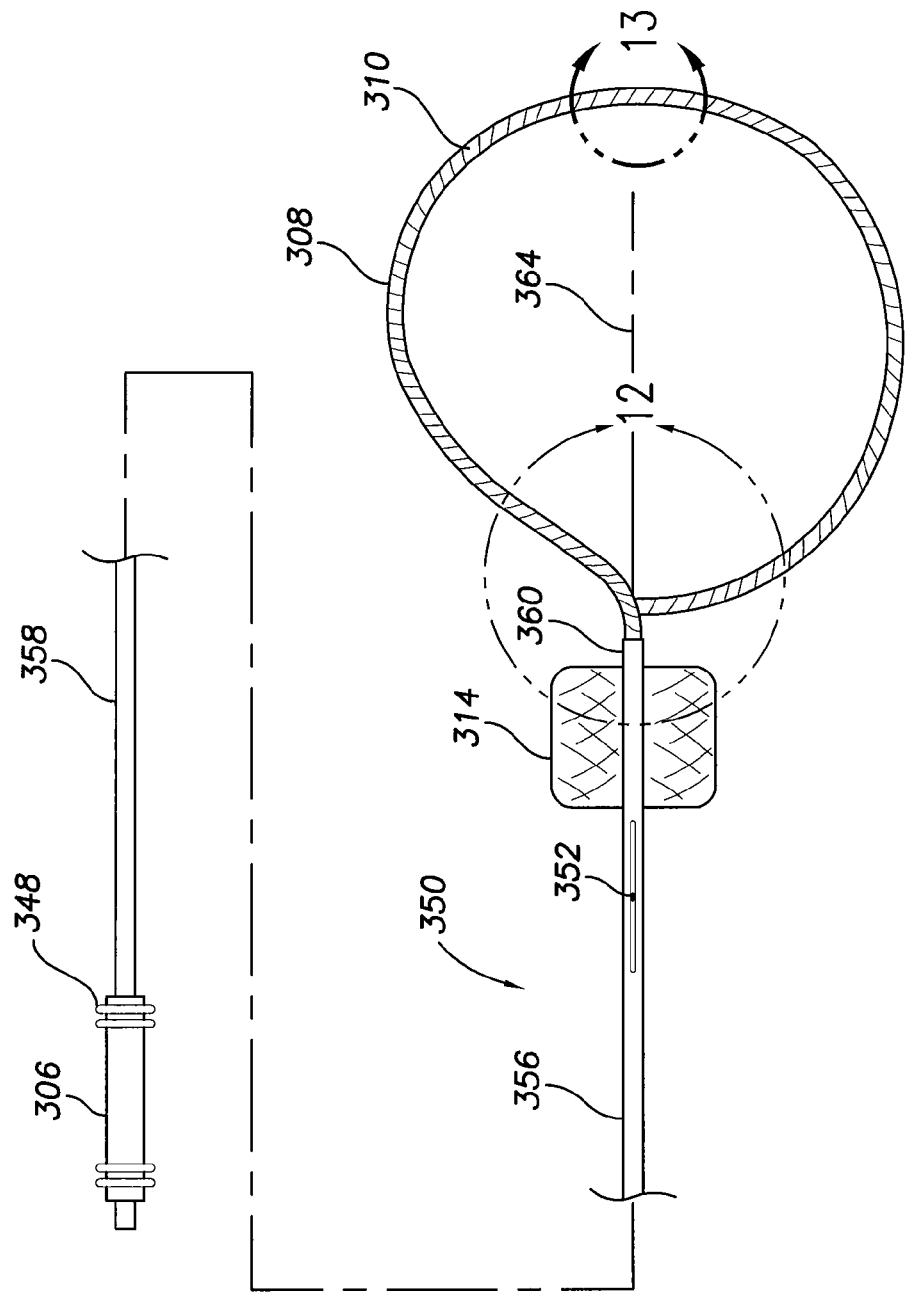
FIG. 10 is a top view of an embodiment of an electrical lead.
Figure 11:
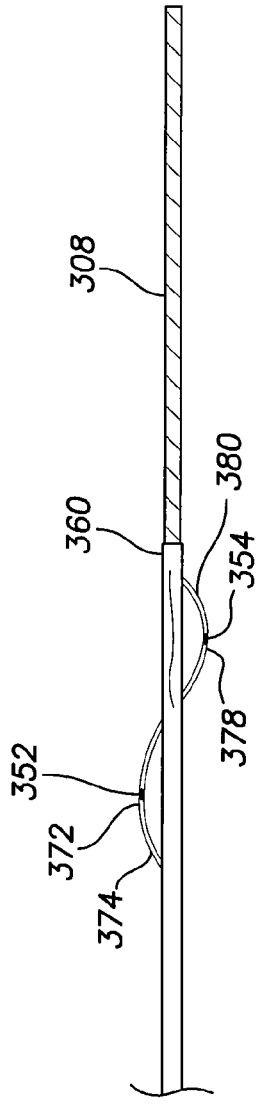
FIG. 11 is a side view of a distal portion of the electrical lead of FIG. 10.
Figure 14:
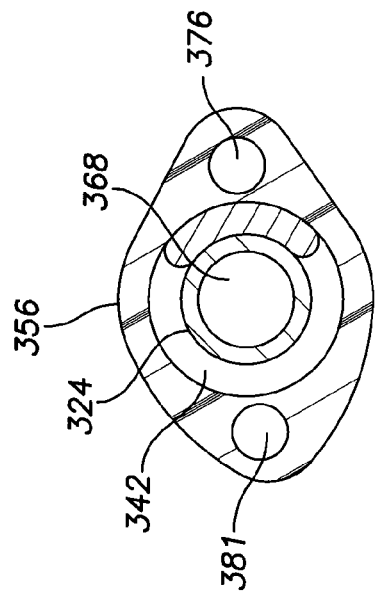
FIG. 14 is a transverse cross sectional view of the electrical lead of FIG. 12 taken along lines 14-14 of FIG. 12.
Figure 13:
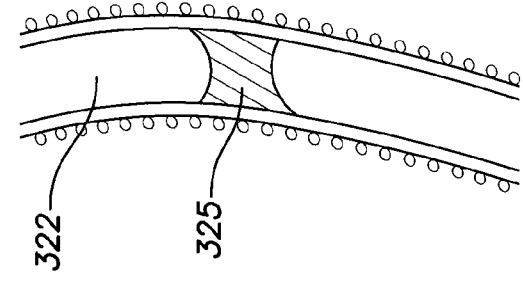
FIG. 13 is an enlarged view in section of the encircled portion 13-13 in FIG. 10.
Figure 12:
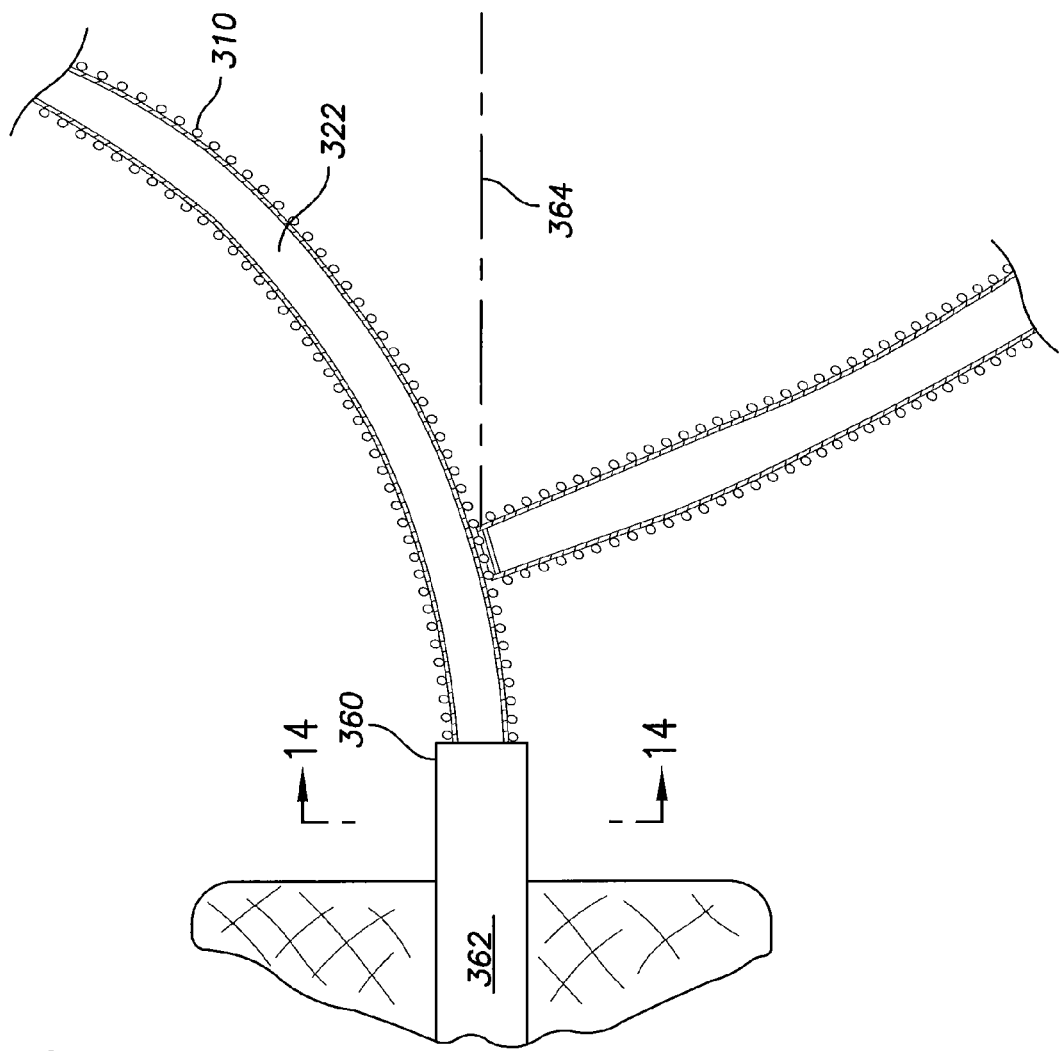
FIG. 12 is an enlarged view in partial section of the electrical lead of FIG. 10 indicated by the encircled portion 12-12 of FIG. 10.

The distal electrode 310 disposed on the distal loop 308 has sufficient surface area for delivering shocking pulses of electrical energy to a patient's heart. That is, some embodiments of the distal electrode 310 may be relatively large surface area electrodes used for applying shocking electrical energy pulses to target tissue without burning the target tissue of the patient and may have a surface area of about 100 $mm^2$ to about 5000 $mm^2$. For some embodiments, the distal electrode 310 may be an exposed electrode coil that is disposed over the tubular member 324 of the distal loop 308 and extend around an entire circumference of the resilient distal loop 308 as shown in FIG. 5. The distal electrode coil 310 may be a monofilar or multifilar coil and may be made from a highly conductive and resilient material such as MP35N, stainless steel, Elgiloy®, platinum or the like. The filament or filaments of some electrode coil embodiments 310 may have a nominal transverse dimension or diameter of about 0.001 inch to about 0.010 inch.

A first pacing electrode 328 having a small surface area relative to the distal electrode 310 is disposed radially outward from the longitudinal axis 317 of the distal portion 316 of the lead body 304 in a direction substantially perpendicular to a plane of the distal loop 308. A second pacing electrode 330 also having a small surface area relative to the distal electrode 310 is disposed radially outward from the longitudinal axis 317 of the distal portion 316 of the lead body 304 in a direction substantially perpendicular to a plane of the distal loop 308 and opposite that of the first pacing electrode 328. For the electrical lead embodiment 302 shown in FIGS. 5-9, the first and second pacing electrodes 328 and 330 are disposed distally of the distal end 312 of the elongate lead body 304 within or otherwise encompassed by the distal loop 308 or an imaginary cylinder defined by the distal loop 308 (not shown). The pacing electrodes 328 and 330 are annular electrodes disposed on a flexible resilient shaft 332 that has a preformed shape assuming the "S-shaped" or serpentine configuration shown in FIG. 6 when in a relaxed state. The serpentine pattern of the resilient shaft 332 produces a smooth atraumatic platform having a first apex 334 on one side of the distal loop 308 and a second apex 336 on a second or opposite side of the distal loop 308. The first pacing electrode 328 is disposed on or near the first apex 332 and the second pacing electrode 330 is disposed on or near the second apex 336. Such an arrangement, when disposed within a confined space between two surfaces, such as the pericardial space, will promote contact of either or both the first pacing electrode 328 and second pacing electrode 330 with surface tissue. Disposing this particular embodiment within the pericardial space of a patient promotes direct contact of one of the pacing electrodes 328 or 330 with the epicardial surface of the patient's heart and contact with the pericardial sac with the opposite pacing electrode 328 or 330. Some embodiments of the pacing electrodes 328 and 330 are relatively small surface area annular electrodes that may be used for pacing, sensing or the like and may have a surface area of about 2 $mm^2$ to about 20 $mm^2$.

For some embodiments one or more of the electrodes 310, 328 and 330, discussed above, may include a thin low polarization coating (not shown) in order to improve the transmission of therapeutic energy from the electrode to target tissue. Such low polarization coatings may be selected from low polarization coatings materials such as nitrides, carbides and carbonitrides. One useful low polarization coating is a porous layer of titanium nitride. The electrodes may also include a highly conductive and radiopaque coating such as gold, platinum, titanium, alloys thereof or the like.

The proximal connector 306 disposed at the proximal end 307 of the lead body 304 and has a conductive terminal that corresponds and is electrically coupled to each electrode 310, 328 and 330. The distal coil electrode 310 is electrically coupled to a proximal tubular terminal 338 disposed on a proximal end 340 of the connector 306 by an elongate conductor, which may be a coiled conductor 342, disposed and in electrical communication between the distal coil electrode 310 and the proximal tubular terminal 338. The elongate conductor 342 may be coated with an insulative coating along some or all of its length. The multi-lumen shaft 318 of the elongate lead body 304, and the inner lumens thereof, may also be made of a flexible insulative material that may be used to electrically insulate one or more of the conductors along some length thereof. The proximal tubular terminal 338 has an inner lumen 344 which is in fluid communication with an inner lumen 346 of the connector 306 which is, in turn, in fluid communication with the main inner lumen 320 of the shaft 318 of the lead body 304. The connector 306 also includes several annular deformable seals 348 disposed about an outside surface of the connector 306 such that the connector 306 is configured to be sealingly and electrically coupled to the receptacle 309 of the stimulation device 10.

Additional elongate conductors are disposed and in electrical communication between the first pacing electrode 328, the second pacing electrode 330 and respective annular conductive terminals disposed on the proximal connector 306. For some embodiments, the elongate conductors disposed between and in electrical communication with the pacing electrodes 328 and 330 and the respective conductive terminals of the connector are insulated conductor cables which may non-coiled or coiled. Coiled embodiments of the elongate conductors may be monofilar or multifilar coils.

As discussed above, the electrical lead 302 may also include a tissue fixation element 314 disposed on the distal portion 316 of the lead body 304 adjacent the distal loop 308. The tissue fixation element 314 lies in a plane substantially parallel to the plane formed by the distal loop 308. For some embodiments, the tissue fixation element 314 may be one or more patches of porous thrombogenic material such as polyester mesh, and may have a surface area of at least about 50 mm². The porous material of the tissue fixation element 314 allows or promotes tissue in-growth or other tissue fixation mechanisms, such as thrombogenic fixation, into the tissue fixation element 314 after deployment of the distal loop 308 and tissue fixation element 314 to target tissue within a patient's body. The pore size for a mesh of some tissue fixation element embodiments 314 that allows tissue in-growth may be at least about 5 microns to about 20 microns. Although the tissue fixation element embodiment 314 is shown disposed on the distal portion 316 of the lead body 304, other tissue fixation element embodiments 314 may serve the same purpose if they are secured to and extend from a portion of the electrical lead 302 that will be disposed within or adjacent tissue when the lead 302 is deployed within a patient's body. It may also be desirable to have the tissue fixation element or elements 314 secured to and extending from a position adjacent an electrode of the lead 302. As such, the tissue fixation element 314 may also be disposed on the distal loop 308, the resilient shaft 332 or any other suitable site on the lead 302.

FIGS. 10-14 illustrate another embodiment of an electrical lead 350 that is similar in many respects to the electrical lead 302 shown in FIGS. 5-9. The electrical lead 350 is substantially the same as the electrical lead 302 except that the first pacing electrode 352 and second pacing electrode 354 of the electrical lead 350 are disposed proximally of the distal loop 308 of the electrical lead 350 and extend from a multi-lumen shaft 356 of an elongate lead body 358. The lead body 358 has a distal end 360, a distal portion 362 and a longitudinal axis 364 of the distal portion 362. The multi-lumen shaft 356 has a main inner lumen 368 extending the length thereof which is in fluid communication with the shaping lumen 322 of the distal loop 308. The multi-lumen shaft 356 has a slightly different configuration from that of the multi-lumen shaft 318 discussed above in order to accommodate the arrangement of the pacing electrodes 352 and 354. In particular, the multi-lumen shaft 356 has two lumens for carrying the conductors of the pacing electrodes 352 and 354 disposed on opposite sides of the multi-lumen shaft 356. The resilient distal loop 308 embodiment has a closed configuration that extends from the distal end 360 of the lead body 358 and is configured to resiliently resume a looped shape after being straightened for deployment within a patient's body.

The first pacing electrode 352 is disposed on or near an apex 372 of a first resilient member 374 extending from a first lumen 376 of the multi-lumen shaft 356 of the elongate lead body 358. The apex 372 of the first resilient member 374 extends away from the longitudinal axis 364 of the distal portion 362 of the lead body 358 in a direction substantially perpendicular to a plane formed by the distal loop 308. An apex 378 of a second resilient member 380 extends away from the longitudinal axis 364 of the distal portion 362 of the lead body 358 in a direction substantially perpendicular to a plane formed by the distal loop 308 and substantially opposite the direction of the first resilient member 374. The second resilient member 380 extends from a second lumen 381 of the multi-lumen shaft 356. The second pacing electrode 354 is disposed on or near the apex 378 of the second resilient member 380. For some embodiments, the resilient members 374 and 380 extend a distance of about 0.5 mm to about 5 mm from an outer surface of the lead body 358. The apices 372 and 378 of the resilient members 374 and 380, respectively, may be compressed radially inwardly during delivery of the electrical lead 350 or while confined between tissue surfaces within a patient's body such as the epicardial surface and pericardial surface of a patient's heart tissue. Once compressed, the resilient members 374 and 380 will tend to resume their relaxed configuration and apply an outward radial force so as to promote contact by respective pacing electrodes 352 and 354 disposed thereon with the constraining tissue surfaces. Disposing this particular embodiment within the pericardial space of a patient promotes direct contact of one of the pacing electrodes 352 and 354 with the epicardial surface of the patient's heart and contact with the pericardial sac with the opposite pacing electrode.

In order to apply therapeutic electrical energy to target tissue of a patient, it may be desirable to deploy an electrical lead embodiment discussed above to a specific area of a patient's heart by non-invasive methods. In particular, it may be desirable to deploy an electrical lead with the electrodes of the lead disposed in a pericardial space of a patient's heart by non-invasive techniques. FIGS. 15-20 illustrate a method embodiment of deploying an electrical lead within the pericardial space of a patient's heart using a subxiphoid approach.

Figure 15:
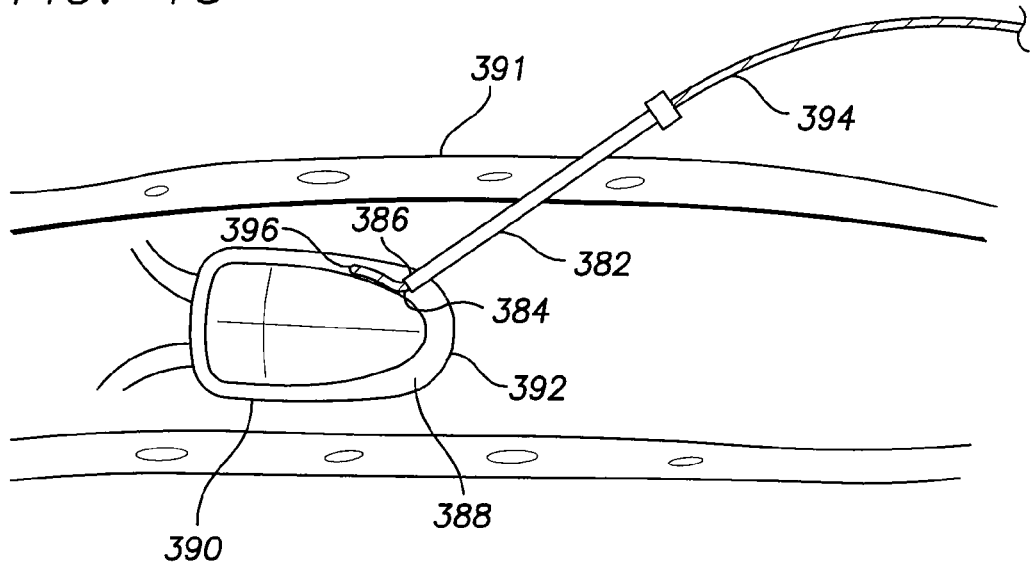
FIG. 15 shows a distal end of a needle disposed within a pericardial space of a patient's heart with a distal portion of a guidewire extending from a distal port of the needle into the pericardial space.
Figure 16:
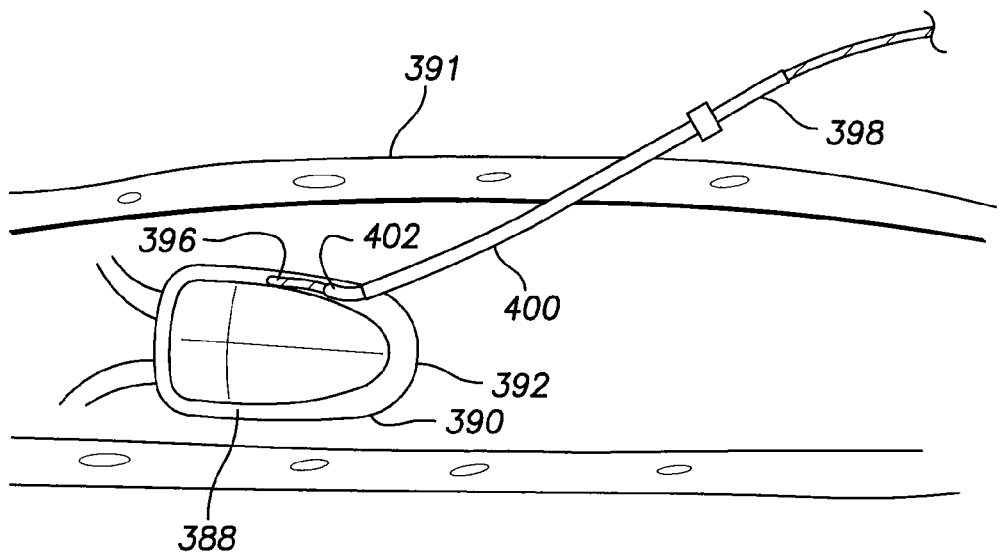
FIG. 16 shows a distal end of an introducer sheath and distal end of a dilator disposed within an inner lumen of the introducer sheath disposed within the pericardial space of the patient's heart with an inner lumen of the dilator disposed over the guidewire.
Figure 17:
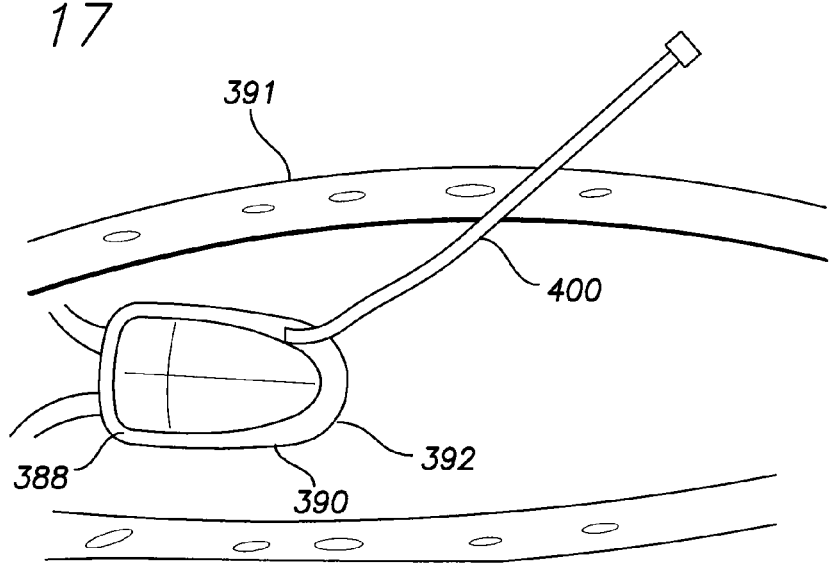
FIG. 17 is a side view of a patient's chest cavity with the distal end of the introducer sheath disposed within the intrapericardial space of the patient's heart with the guidewire and dilator shown in FIG. 16 withdrawn.

Referring to FIG. 15, a needle, such as a Toughy needle 382, is shown having a sharpened tissue penetrating distal end 384 and distal port 386 disposed within a pericardial space 388 of the patient's heart 390 having passed through the patient's chest wall 391 and an access hole formed in the pericardium. This type of access may be achieved by the distal end 384 of the needle 382 through the patient's chest and pericardial sac 392 of the patient's heart 390. Thereafter, a guidewire 394 configured to pass through an inner lumen of the needle 382 is advanced through the inner lumen of the needle 382 until a distal end 396 or distal portion of the guidewire 394 is disposed within the pericardial space 388. A dilator 398 which is configured to be advanced over the guidewire 394 and introducer sheath 400 which is disposed over the dilator 398 are then advanced over the guidewire 394 such that a distal end 402 of the dilator 398 and distal port of the introducer sheath 400 are disposed within the pericardial space 388 as shown in FIG. 16. The dilator 398 and guidewire 394 may then be withdrawn from the introducer sheath 400 leaving the inner lumen of the introducer sheath 400 positioned to function as an access canal from a location outside the patient's body to the pericardial space 388 of the patient as shown in FIG. 17.

Figure 18:
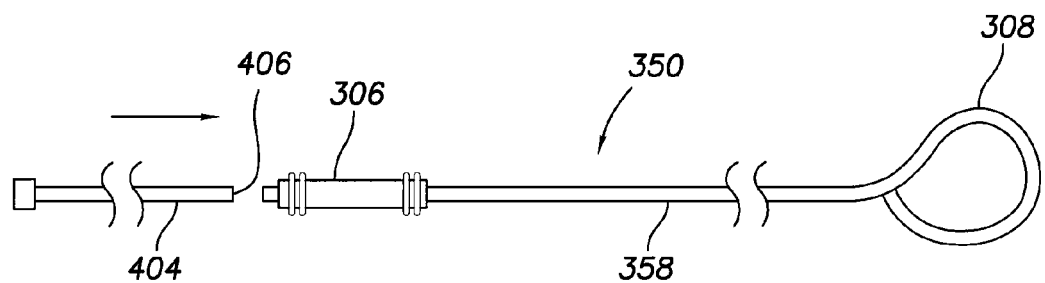
FIG. 18 is a top view of an electrical lead and a stylet being inserted into an inner lumen of the lead body.
Figure 19:
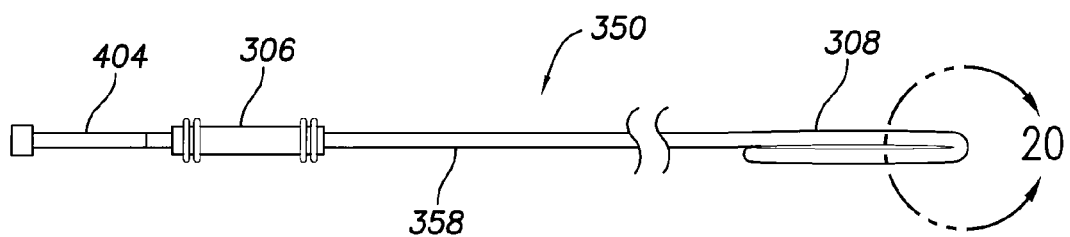
FIG. 19 shows the electrical lead of FIG. 18 with the stylet completely inserted into the inner lumen of the lead body and shaping lumen of the distal loop.
Figure 20:
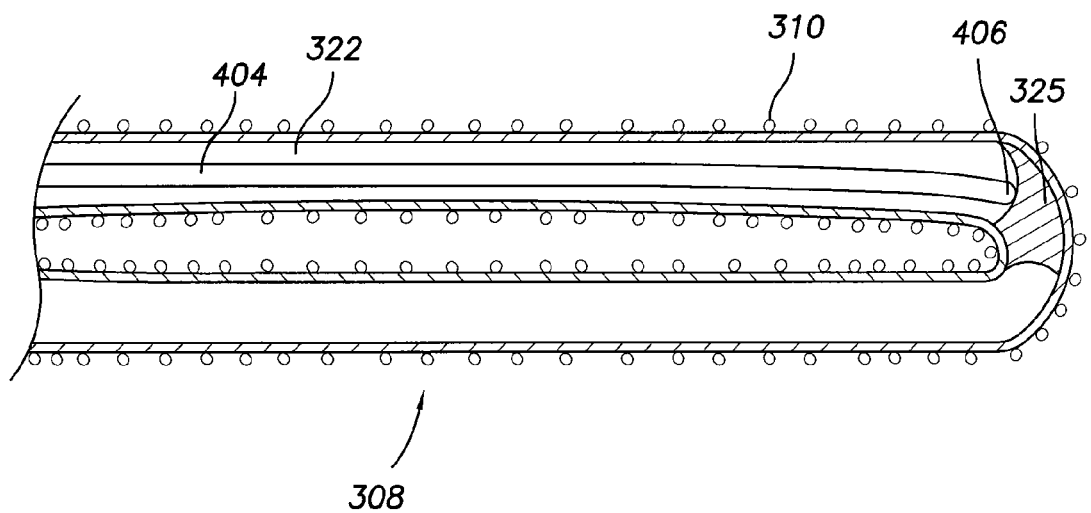
FIG. 20 is an enlarged view in section of the encircled portion of the distal loop of FIG. 17 indicated by the encircled portion 20-20 of FIG. 19.

Once an access canal is achieved to the pericardial space 388 of the patient, an electrical lead embodiment, such as electrical leads 302 and 350, may be prepared for deployment and advanced through the inner lumen of the introducer sheath 400 and into the pericardial space 388. In order to prepare the electrical lead 350 for advancement through the inner lumen of the introducer sheath 400, a stylet 404 is advanced into the shaping lumen 322 of the electrical lead 350 as shown in FIGS. 18-20. In order to reach the shaping lumen 322, the stylet 404 may be passed through the inner lumen 346 of the connector 306 and inner lumen 368 of the elongate lead body 358 first. Once the stylet 404 is disposed within the shaping lumen 322 and comes to the stop member 325 disposed within a distal portion 326 of the shaping lumen 322, the shaping lumen 322 and distal loop 308 as a whole assume a substantially straightened configuration having a relatively low transverse profile suitable for advancing through the inner lumen of the introducer sheath 400 as shown in FIGS. 19 and 20.

The distal loop 308 is nominally configured as a resilient structure that forms a substantially circular or elliptical shape for some embodiments when the distal loop 308 is in a relaxed state. So long as the stylet 404 has sufficient longitudinal stiffness to overcome the resiliency of the distal loop 308, the distal loop 308 will assume the substantially straightened configuration of the distal portion of the stylet 404 shown in FIGS. 19 and 20 once the stylet 404 is disposed within the shaping lumen 322. The optional stop 325 member disposed within the shaping lumen 322 may help to distribute the force applied by the distal end 406 of the stylet 404 to the distal loop 322 to provide a positive stopping point for axial advancement of the stylet 404 and to prevent kinking or damage to the stylet 404 or distal loop 308. In addition to straightening the distal loop 308, the stylet 404 may also provide additional column strength to the electrical lead body 358 and distal loop 308 to assist with pushing the electrical lead 350 through the introducer sheath 400 and for manipulating the position of the distal loop 308 within the pericardial space 388 or other target tissue region once deployed.

Figure 21:
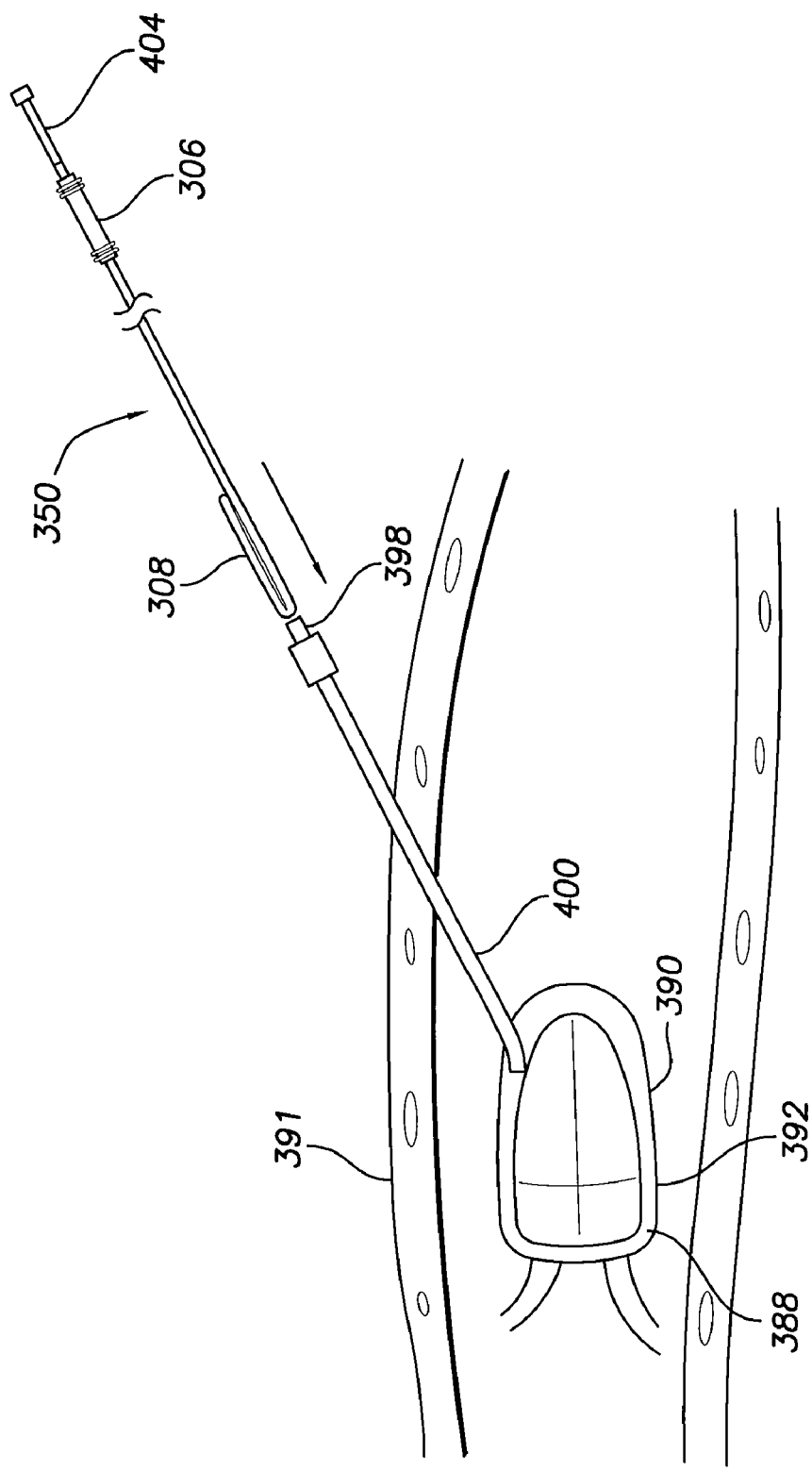
FIG. 21 shows the shaped electrical of FIG. 19 being advanced into the introducer sheath and patient's chest cavity shown in FIG. 15.
Figure 22:
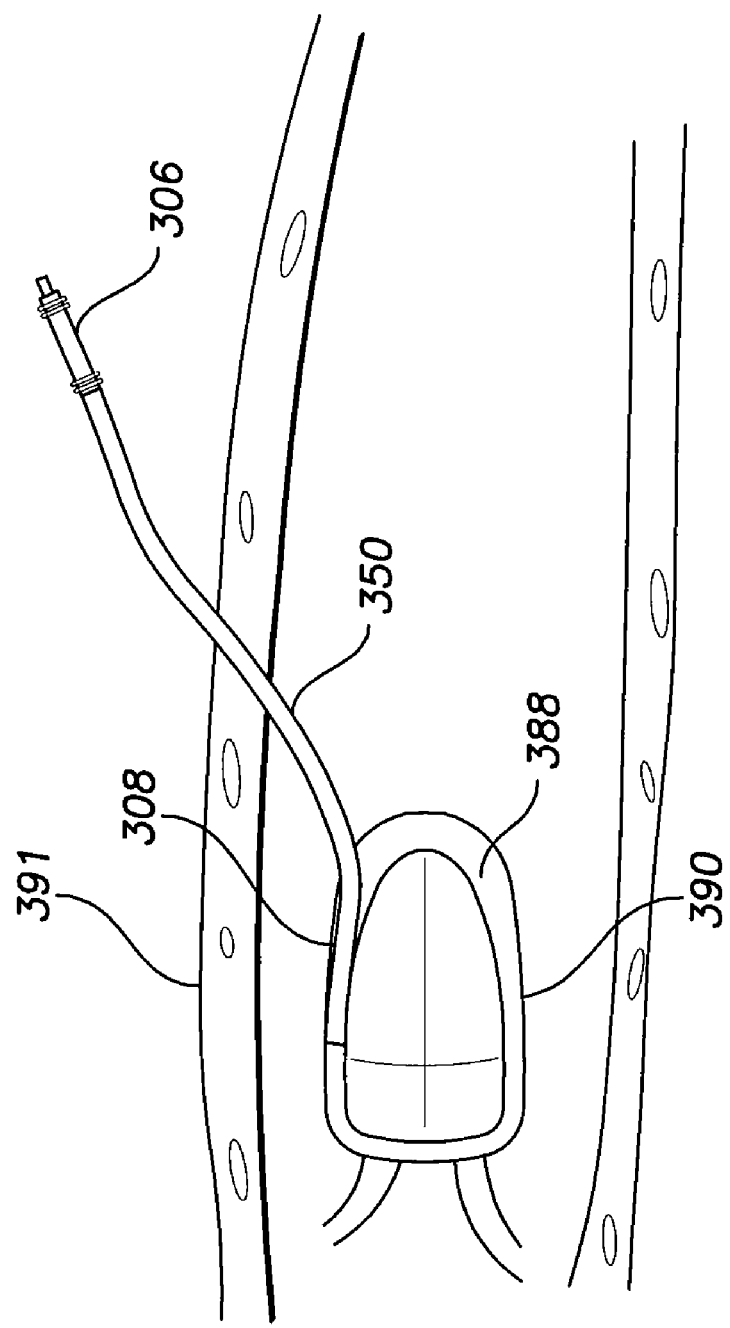
FIG. 22 shows the electrical lead disposed within the intrapericardial space of the patient's heart with the introducer sheath removed.

Once the stylet 404 is disposed within the shaping lumen 322 of the electrical lead 350, the distal end of the electrical lead 350 is inserted into the proximal end of the inner lumen of the introducer sheath 400 as shown in FIG. 21. The electrical lead 350 is then advanced through the introducer sheath 400 and into the patient's pericardial space 388. As the straightened electrical lead 350 is being advanced into the introducer sheath 400, the resilient members 374 and 380, upon which the respective pacing electrodes 352 and 354 are disposed, are compressed in an inward radial direction relative to the longitudinal axis 364 of the elongate lead body 358 in order to fit within the inner lumen of the introducer sheath 400. Once the resilient members 374 and 380 exit the distal port of the introducer sheath 400 in the pericardial space 388, they expand in an outward radial direction due to their resiliency until they achieve their original relaxed configuration or the expansion is checked by contact with target tissue. The introducer sheath 400 may then be withdrawn proximally from the patient's pericardial space 388 and chest as shown in FIG. 22.

Figure 23:
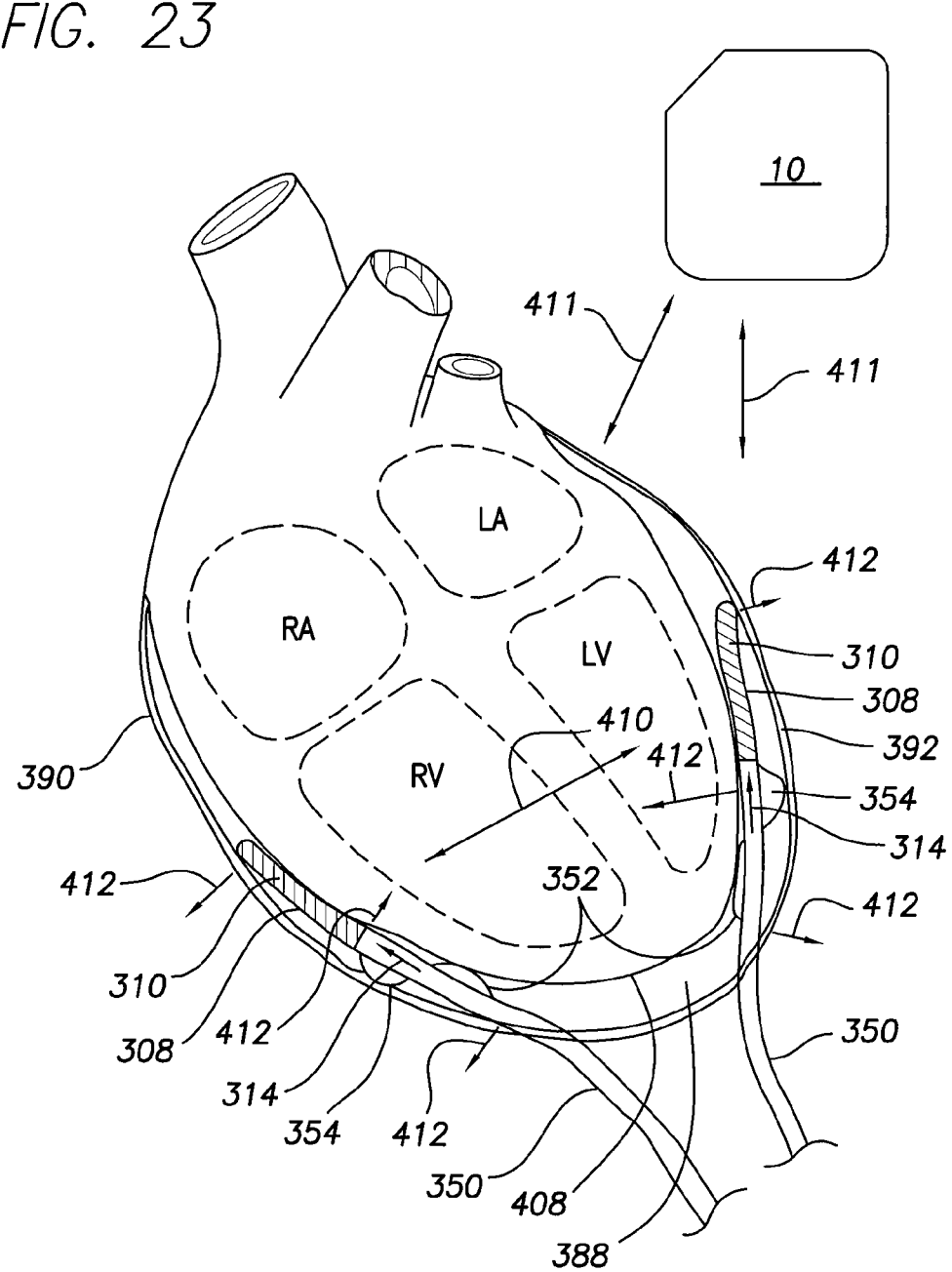
FIG. 23 is a sectional view of a patient's heart showing a pair of electrical lead embodiments disposed in a patient's intrapericardial space.

FIG. 23 shows the distal loop 308, distal coil electrode 310, first pacing electrode 352, second pacing electrode 354 and tissue fixation element 314 of two electrical leads 350 all disposed within the pericardial space 388 on opposite sides of the patient's heart 390. As shown, the distal electrode coil 310 of each electrical lead 350 is making contact over at least a portion thereof with the epicardial tissue surface 408 of the patient's heart 390. In addition, one of the pacing electrodes 352 or 354 of each electrical lead 350 is making resilient contact with epicardial tissue 408 of the patient's heart 390 and a second pacing electrode 352 or 354 opposite the first is shown making contact with pericardial tissue 392. Once the electrical lead or leads 350 have been deployed such that one or more of the electrodes 310, 352 or 354 are in contact with or near desired target tissue, a therapeutic electrical signal may be transmitted from the stimulation device 10, which is in electrical communication with the electrical lead 350, to one or more of the electrodes 310, 352 or 354 and adjacent target tissue of the patient.

Such a deployment of multiple electrical leads 350 may be used to deliver therapeutic electrical signals in a variety of configurations. For example, defibrillation shocking signals may be transmitted in a bipolar fashion between one distal coil electrode 310 and the other distal coil electrode 310 of the electrical leads 350 as represented by arrow 410 in FIG. 23. Such shocking signals may also be transmitted between the stimulation device 10 and either or both of the distal coil electrodes 310 of the electrical leads 350 as shown by arrows 411. A similar variety of configurations may be used to deliver therapeutic energy signals from the first and second pacing electrodes 352 and 354. In addition, a similar variety of configurations may be used to receive sensed energy signals from target tissue through the first and second pacing electrodes 352 and 354. For some embodiments, after deployment of the electrical lead or leads 350, the conduction of each pacing electrode 352 and 354 is tested and the pacing electrode 352 or 354 with better electrical communication with the epicardial surface 408 then selected for delivering an electrical pacing signal or signals. The other pacing electrode 352 or 354 that is not selected for pacing may then be used for sensing signals emitted from adjacent target tissue.

For electrical lead embodiments, such as electrical lead 302 and electrical lead 350, that include a tissue fixation element 314, the deployment method embodiments discussed above may further include advancing the distal end of the electrical lead into the pericardial space 388 until the tissue attachment element 314 is disposed within the pericardial space 388 and allowing body tissue of the patient to attach to the tissue fixation element 314. In this way, once the electrical lead is deployed adjacent to target tissue within the pericardial space 388 or at some other desired location within a patient's body, the operator need only maintain the electrical lead in the desired position for a predetermined period of time in order for the distal loop 308, distal coil electrode 310 or both to be fixed relative to the target tissue. For some tissue fixation element 314 materials, the time required for body tissue to secure to the tissue fixation element 314 may be about 5 minutes to about 30 minutes. The fixation of the distal loop 308 of the lead body relative to target tissue may also be accomplished or augmented by substantially static frictional forces between contact points of the distal loop 308 and lead body 304 or 358 with tissue. For the embodiments shown in FIG. 23, the distal loops 308 of the deployed electrical leads 350 are configured to lie substantially in a plane when in a relaxed state. The pericardial space 388 is curved, and, as such, imparts a deforming force or forces on the distal loop 308. The distal loop 308 resists these deforming forces with opposing resilient forces as indicated by arrows 412 shown in FIG. 23.

In addition to the subxiphoid deployment method discussed above, it may also be desirable to deploy some of the lead embodiments discussed herein by a transvenous approach. For example, U.S. Pat. No. 4,998,975 (Cohen et al.), Ser. No. 429,440, filed Oct. 30, 1989, describes useful transvenous deployment methods and is incorporated by reference herein in its entirety.

In general, a wide variety of techniques can be implemented consistent with the principles the invention and no attempt is made herein to describe all possible techniques. Although described primarily with reference to embodiments wherein the implanted stimulation device is a defibrillation/pacer, the principles discussed herein are applicable to other implantable medical devices as well. The various functional components of the exemplary embodiments may be implemented using any appropriate technology including, for example, microprocessors running software programs or application specific integrated circuits (ASICs) executing hard-wired logic operations. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. An implantable electrical lead, comprising:
an elongate flexible lead body having a distal end, a distal portion and an inner lumen extending therethrough;
a resilient distal loop extending from the distal end of the lead body, the distal loop having a permanently closed configuration and configured to resiliently resume an expanded closed-loop shape after being straightened into a collapsed closed-loop shape for deployment within a patient's body, wherein the distal loop in a relaxed non-deformed state lies substantially within a plane;
a shaping lumen extending through at least one side of the distal loop in fluid communication with the inner lumen of the lead body;
a stop disposed in the shaping lumen and configured to block further advancement of a stylet through the shaping lumen;
a distal defibrillation electrode disposed on the distal loop;
a proximal connector disposed at a proximal end of the lead body having a conductive terminal and an inner lumen in fluid communication with the inner lumen of the lead body;
an elongate conductor disposed and in electrical communication between the distal electrode and a conductive terminal disposed on the proximal connector; and
a flexible resilient shaft extending from the distal end of the lead body so as to extend into the area bounded by the closed configuration of the distal loop, the shaft having a preformed shape defining a first apex on a first side of the plane of the distal loop and a second apex an a second side of the plane of the distal loop opposite the first side of the distal loop.

2. The lead of claim 1 further comprising a first pacing electrode located on or near the first apex and a second pacing electrode located on or near the second apex.

3. The lead of claim 1 further comprising a tissue fixation element disposed on a distal portion of the lead.

4. The lead of claim 1 wherein the elongate conductor comprises a coiled conductor.

5. The lead of claim 1 wherein the elongate conductor comprises a multifilar coiled conductor.

6. The lead of claim 1 wherein the distal defibrillation electrode comprises an exposed electrode coil.

7. The lead of claim 1 wherein the surface area of the distal defibrillation electrode is about 100 mm$^2$ to about 5000 mm$^2$.

8. The lead of claim 1 wherein the distal defibrillation electrode further comprises a low polarization coating.

9. The lead of claim 1 wherein the distal defibrillation electrode further comprises a highly electrically conductive radiopaque outer surface material.

10. The lead of claim 1 wherein the circumference of the resilient distal loop is about 100 mm to about 400 mm.

11. The lead of claim 1 wherein the distal loop in a relaxed non-deformed state lies substantially within a plane.

12. An implantable electrical lead, comprising:
an elongate flexible lead body having a distal end, a distal'portion and an inner lumen extending therethrough;
a resilient distal loop extending from the distal end of the lead body, the distal loop having a permanently closed configuration and configured to resiliently resume an expanded closed-loop shape after being straightened into a collapsed closed-loop shape for deployment within a patient's body, wherein the distal loop in a relaxed non-deformed state lies substantially within a plane;
a shaping lumen extending through at least one side of the distal loop in fluid communication with the inner lumen of the lead body;
a stop disposed in the shaping lumen and configured to block further advancement of a stylet through the shaping lumen;
a distal defibrillation electrode disposed on the distal loop;
a proximal connector disposed at a proximal end of the lead body having a conductive terminal and an inner lumen in fluid communication with the inner lumen of the lead body;
an elongate conductor disposed and in electrical communication between the distal defibrillation electrode and a conductive terminal disposed on the proximal connector;
a first flexible resilient member extending from a first region of the lead body proximal the distal end of the lead body and having a preformed shape defining a first apex on a first side of the plane of the distal loop; and
a second flexible resilient member extending from a second region of the lead body proximal the first region of the lead body and having a preformed shape defining a second apex on a second side of the plane of the distal loop opposite the first side of the distal loop.

13. The lead of claim 12 further comprising a first pacing electrode located on or near the first apex and a second pacing electrode located on or near the second apex.

14. The lead of claim 12 wherein each of the first flexible resilient member and the second flexible resilient member comprise a lumen in communication with a lumen of the flexible lead body.

15. The lead of claim 12 further comprising a tissue fixation element disposed on a distal portion of the lead.

16. The lead of claim 12 wherein the elongate conductor comprises a coiled conductor.

17. The lead of claim 12 wherein the elongate conductor comprises a multifilar coiled conductor.

18. The lead of claim 12 wherein the distal defibrillation electrode comprises an exposed electrode coil.

19. The lead of claim 12 wherein the surface area of the distal defibrillation electrode is about 100 mm$^2$ to about 5000 mm$^2$.

20. The lead of claim 12 wherein the distal defibrillation electrode further comprises a low polarization coating.

21. The lead of claim 12 wherein the distal defibrillation electrode further comprises a highly electrically conductive radiopaque outer surface material.

22. The lead of claim 12 wherein the circumference of the resilient distal loop is about 100 mm to about 400 mm.

23. The lead of claim 12 wherein the distal loop in a relaxed non-deformed state lies substantially within a plane.

* * * * *